United States Patent
Bode et al.

(10) Patent No.: US 9,296,730 B2
(45) Date of Patent: Mar. 29, 2016

(54) AURORA KINASE INHIBITORS

(71) Applicant: REGENTS OF THE UNIVERSITY OF MINNESOTA, Minneapolis, MN (US)

(72) Inventors: Ann M. Bode, Minneapolis, MN (US); Zigang Dong, Minneapolis, MN (US); Kanamata Reddy, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/434,712

(22) PCT Filed: Oct. 25, 2013

(86) PCT No.: PCT/US2013/066944
§ 371 (c)(1),
(2) Date: Apr. 9, 2015

(87) PCT Pub. No.: WO2014/066840
PCT Pub. Date: May 1, 2014

(65) Prior Publication Data
US 2015/0232456 A1  Aug. 20, 2015

Related U.S. Application Data

(60) Provisional application No. 61/719,215, filed on Oct. 26, 2012.

(51) Int. Cl.
C07D 405/06 (2006.01)
C07D 209/34 (2006.01)
A61K 31/4015 (2006.01)

(52) U.S. Cl.
CPC .......... *C07D 405/06* (2013.01); *A61K 31/4015* (2013.01); *C07D 209/34* (2013.01)

(58) Field of Classification Search
CPC . C07D 405/06; C07D 209/34; A61K 31/4015
See application file for complete search history.

(56) References Cited

U.S. PATENT DOCUMENTS

| 6,133,305 | A  | 10/2000 | Tang et al. |
| 7,897,602 | B2 | 3/2011  | Huang et al. |
| 2004/0102509 | A1 | 5/2004 | Andrews et al. |
| 2010/0087464 | A1 | 4/2010 | Mi et al. |

FOREIGN PATENT DOCUMENTS

| WO | 9501349 A1   | 1/1995 |
| WO | 0008202 A2   | 2/2000 |
| WO | 2006052936 A2 | 5/2006 |
| WO | 2011096676 A2 | 8/2011 |

OTHER PUBLICATIONS

Beccalli et al. (J. Chem. Soc. Perkin Trans., 1994, 579-587).*
Xie et al. (Mol Cancer Ther; 2013, 12(6); 950-8).*
Andrews, "Aurora kinases: shining lights on the therapeutic horizon?" Oncogene 24(32), 5005-5015 (2005).
Barr et al., "Aurora-A: the maker and breaker of spindle poles", J Cell Sci, 120(Pt 17), 2987-2996 (2007).
Beccalli, "Synthesis of the Carbazole Alkaloids Hyellazole and 6-Chlorohyellazole and Related Derivatives", J. Chem. Soc. Perkin Trans. 1, 579-587 (1994).
Carmena et al., "The cellular geography of aurora kinases", Nat Rev Mol Cell Biol, 4(11), 842-854 (2003).
Carvajal et al., "Aurora kinases: new targets for cancer therapy", Clin Cancer Res 12(23), 6869-6875 (2006).
Chen et al., "Overexpression of an Aurora-C kinase-deficient mutant disrupts the Aurora-B/INCENP complex and induces polyploidy", J Biomed Sci 12(2), 297-310 (2005).
Chouhan et al., "Regiospecific Epoxide Opening: A Facile Approach for the Synthesis of 3-Hydroxy-3-Aminomethylindolin-2-one Derivatives", Green Chemistry 13, 2553-2560 (2011).
Ditchfield et al., "Aurora B couples chromosome alignment with anaphase by targeting BubR1, Mad2, and Cenp-E to kinetochores", J Cell Biol 161(2), 267-280 (2003).
Elinson et al. "Electrochemically Induced Henry Reaction of Nitromethane and Carbonyl Compounds" Tetrahedron 64, 5915-5919 (2008).
Gorgun et al., "A novel Aurora-A kinase inhibitor MLN8237 induces cytotoxicity and cell-cycle arrest in multiple myeloma", Blood 115(25), 5202-5213 (2010).
Harrington et al., "VX-680, a potent and selective small-molecule inhibitor of the Aurora kinases, suppresses tumor growth in vivo", Nat Med 10(3), 262-267 (2004).
Hauf et al., "The small molecule Hesperadin reveals a role for Aurora B in correcting kinetochore-microtubule attachment and in maintaining the spindle assembly checkpoint", J Cell Biol 161(2), 281-294 (2003).

(Continued)

*Primary Examiner* — Robert Havlin
(74) *Attorney, Agent, or Firm* — Viksnins Harris & Padys PLLP

(57) ABSTRACT

The invention provides a compound of formula I: or a salt thereof, wherein ring A and $R^1$-$R^4$ have any of the values defined in the specification. The compounds have activity as Aurora B kinase inhibitors and are useful for treating conditions associated with Aurora B kinase activity (e.g. cancer).

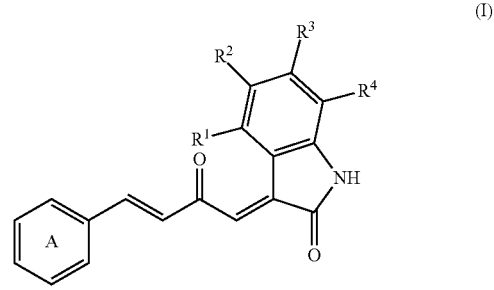

17 Claims, 7 Drawing Sheets

(56) References Cited

OTHER PUBLICATIONS

Jackson et al., "Targeted anti-mitotic therapies: can we improve on tubulin agents?" Nat Rev Cancer, 7(2), 107-117 (2007).

Kallio et al., "Inhibition of aurora B kinase blocks chromosome segregation, overrides the spindle checkpoint, and perturbs microtubule dynamics in mitosis", Curr Biol 12(11), 900-905 (2002).

Kollareddy et al., "Aurora kinase inhibitors: Progress towards the clinic", Invest New Drugs 30(6), 2411-2432 (2012).

Li et al., "Asymmetric Nitroaldol Reactions of Nitroalkanes with Isatins Catalyzed by Bifunctional Cinchona Alkaloid Derivatives", European Journal of Organic Chemistry, vol. 2011 (27), 5237-5241 (2011).

Liu et al., "Catalytic Enantioselective Henry Reactions of Isatines: Application in the Concise Synthesis fo (S)-(-)- Spirobrassinin", Chemistry 17(28), 7791-7795 (2011).

Marumoto et al., "Aurora-A—a guardian of poles", Nat Rev Cancer 5(1), 42-50 (2005).

Meshram et al., "An Efficient and Environmentally Friendly DABCO Catalyzed Henry Reaction of Isatins", Tetrahedron Letters 52, 5862-5864 (2011).

Patent Cooperation Treaty, International Searching Authority, Search Report and Written Opinion for PCT/US2013/066944, 10 pages, Nov. 28, 2013.

Xie et al., "Identification of (E)-3-((E)-4-(benzo[d][1,3]dioxol-5-yl)-2-oxobut-3-en-1-ylidene)indolin-2-one as a novel Aurora B inhibitor both in vitro and in vivo", Cancer Res 73(2), 716-724 (2013).

Yang et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo", Blood 110(6), 2034-2040 (2007).

Chiang et al., "Discovery of Pyrrole-Indolin-2-ones as Aurora Kinase Inhibitors with a Different Inhibition Profile", J. Med. Chem., 53 (16), 5929-5941 (2010).

Liu et al., "Asymmetric cross aldol addition of isatins with α,β-unsaturated ketones catalyzed by a bifunctional Brønsted acid—Brønsted base organocatalyst", Tetrahedron 68, 3843-3850 (2012).

Prakash et al., "Indolin-2-Ones in Clinical Trials as Potential Kinase Inhibitors: A Review", Pharmacology & Pharmacy, 3, 62-71 (2012).

\* cited by examiner

No inhibitor

HCT116 cells

AURORA KINASE INHIBITORS

CROSS-REFERENCE TO RELATED APPLICATIONS

This patent application claims the benefit of priority of U.S. application Ser. No. 61/719,215, filed Oct. 26, 2012, which application is herein incorporated by reference.

STATEMENT OF GOVERNMENT RIGHTS

This invention was made with government support under R37-CA081064, CA120388, ES016548, CA227501, and CN053301 awarded by the National Institutes of Health. The government has certain rights in the invention.

BACKGROUND OF THE INVENTION

Targeting the progression of mitosis is a highly successful strategy for anticancer treatment (Jackson, J. R., et al., Nat Rev Cancer, 2007. 7 (2): p. 107-17). A closely related subgroup of three serine/threonine kinases, the Aurora kinases, are believed to play a key role in protein phosphorylation in mitosis and have been shown to contribute in the development and progression of cancer. In mammals, the Aurora kinase family comprises three members: Aurora A, B and C (Carmena, M. and W. C. Earnshaw, Nat Rev Mol Cell Biol, 2003. 4 (11): p. 842-54). They display distinct roles during mitosis, which are reflected in their subcellular locations and functions. Aurora A is localized at the centrosome from the time of centrosome duplication through mitotic exit. It has been implicated in several processes required for the generation of bipolar spindle apparatus, including centrosome maturation and separation (Andrews, P. D., Oncogene, 2005. 24 (32): p. 5005-15; and Barr, A. R. and F. Gergely, J Cell Sci, 2007. 120 (Pt 17): p. 2987-96). Small molecule inhibition of Aurora A kinase activity causes defects in centrosome separation with the formation of characteristic monopolar spindles (Marumoto, T., D. Zhang, and H. Saya, Nat Rev Cancer, 2005. 5 (1): p. 42-50). Aurora B is localized to the centromeres from the prophase to the metaphase-anaphase transition. Thereafter, it is localized to midzone spindle microtubules during the telophase and subsequently to midbody during cytokinesis. Aurora B is a chromosomal passenger protein in complex with the inner centromere proteins (INCENP), survivin, and borealin. During mitosis, as the "equatorial-kinase", Aurora B is required for histone H3 phosphorylation, chromosome bi-orientation, the spindle assembly checkpoint, and cytokinesis (Kallio, M. J., et al., Curr Biol, 2002. 12 (11): p. 900-5; and Carvajal, R. D., A. Tse, and G. K. Schwartz, Clin Cancer Res, 2006. 12 (23): p. 6869-75). Inhibition of Aurora B kinase activity with small molecules leads to failure in cytokinesis and abnormal exit from mitosis, resulting in endoreduplication, polyploidy cells, and ultimately apoptosis (Hauf, S., et al., J Cell Biol, 2003. 161 (2): p. 281-94; and Ditchfield, C., et al., J Cell Biol, 2003. 161 (2): p. 267-80). Aurora C is also a chromosomal passenger protein considered to have a similar sub-cellular location as Aurora B. It has been described only in mammals, where it is expressed in testis and certain tumor cell lines and localizes to spindle poles during late mitosis (Carmena, M. and W. C. Earnshaw, Nat Rev Mol Cell Biol, 2003. 4 (11): p. 842-54; and Chen, H. L., et al., J Biomed Sci, 2005. 12 (2): p. 297-310).

Inhibition of Aurora kinases had been shown to be an effective strategy for anticancer therapy, and several Aurora inhibitors have been described, including VX-680 (Harrington, E. A., et al., Nat Med, 2004. 10 (3): p. 262-7), Hesperadin (Hauf, S., et al., J Cell Biol, 2003. 161 (2): p. 281-94), AZD1152 (Yang, J., et al., Blood, 2007. 110 (6): p. 2034-40), and MLN8237 (Gorgun, G., et al., Blood, 2010. 115 (25): p. 5202-13.). More than 30 small molecule Aurora kinase inhibitors are currently in different stages of preclinical and clinical development (Kollareddy, M., et al., Invest New Drugs, 2012), however, none have yet been approved by the FDA for clinical use.

Currently there is a need for agents that are useful for treating or preventing cancer.

SUMMARY OF THE INVENTION

A series of compounds have been identified that possess activity as Aurora B kinase inhibitory properties. Accordingly the invention provides a compound of the invention which is a compound of formula I:

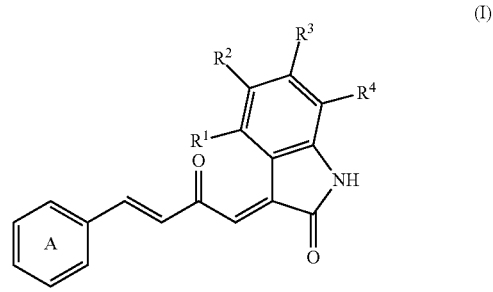

(I)

wherein:

ring A is optionally substituted with one or more groups independently selected from hydroxy, halo, cyano, nitro, ($C_1$-$C_6$)alkyl, ($C_3$-$C_6$)cycloalkyl, ($C_1$-$C_6$)alkoxy, ($C_1$-$C_6$)alkanoyl, ($C_1$-$C_6$)alkoxycarbonyl, methylenedioxy, ethylenedioxy, or ($C_2$-$C_6$)alkanoyloxy, wherein any ($C_1$-$C_6$)alkyl, ($C_3$-$C_6$)cycloalkyl, ($C_1$-$C_6$)alkoxy is optionally substituted with one or more halo;

$R^1$ is H, halo, cyano, nitro, ($C_1$-$C_6$)alkyl, ($C_3$-$C_6$)cycloalkyl, ($C_1$-$C_6$)alkoxy, ($C_1$-$C_6$)alkanoyl, ($C_1$-$C_6$)alkoxycarbonyl, methylenedioxy, ethylenedioxy, or ($C_2$-$C_6$)alkanoyloxy, wherein any ($C_1$-$C_6$)alkyl, ($C_3$-$C_6$)cycloalkyl, ($C_1$-$C_6$)alkoxy is optionally substituted with one or more halo; or $R^1$ and $R^2$ taken together are methylenedioxy or ethylenedioxy;

$R^2$ is H, halo, cyano, nitro, ($C_1$-$C_6$)alkyl, ($C_3$-$C_6$)cycloalkyl, ($C_1$-$C_6$)alkoxy, ($C_1$-$C_6$)alkanoyl, ($C_1$-$C_6$)alkoxycarbonyl, methylenedioxy, ethylenedioxy, or ($C_2$-$C_6$)alkanoyloxy, wherein any ($C_1$-$C_6$)alkyl, ($C_3$-$C_6$)cycloalkyl, ($C_1$-$C_6$)alkoxy is optionally substituted with one or more halo; or $R^1$ and $R^2$ taken together are methylenedioxy or ethylenedioxy; or $R^2$ and $R^3$ taken together are methylenedioxy or ethylenedioxy;

$R^3$ is H, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo; or $R^2$ and $R^3$ taken together are methylenedioxy or ethylenedioxy; or $R^3$ and $R^4$ taken together are methylenedioxy or ethylenedioxy; and $R^4$ is H, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo; or $R^3$ and $R^4$ taken together are methylenedioxy or ethylenedioxy;

or a salt thereof.

The invention also provides a pharmaceutical composition comprising a compound of formula I or a pharmaceutically acceptable salt thereof, and a pharmaceutically acceptable excipient.

The invention also provides a method for treating or preventing cancer in an animal comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of cancer.

The invention also provides a method of inhibiting Aurora B kinase in an animal in need of such treatment comprising administering a compound of formula I, or a pharmaceutically acceptable salt thereof, to the animal.

The invention also provides a method of treating a pathological condition associated with Aurora B kinase in an animal comprising administering an effective Aurora B kinase inhibitory amount of a compound of formula I, or a pharmaceutically acceptable salt thereof, to the animal.

The invention also provides a compound of formula I, or a pharmaceutically acceptable salt thereof, for the prophylactic or therapeutic inhibition of Aurora B kinase.

The invention also provides a compound of formula I, or a pharmaceutically acceptable salt thereof, for the prophylactic or therapeutic treatment of a pathological condition associated with Aurora B kinase The invention also provides the use of a compound of formula I, or a pharmaceutically acceptable salt thereof to prepare a medicament for inhibiting Aurora B kinase in an animal.

The invention also provides the use of a compound of formula I, or a pharmaceutically acceptable salt thereof, to prepare a medicament for treating a pathological condition associated with Aurora B kinase in an animal.

The invention also provides processes and intermediates disclosed herein that are useful for preparing a compound of formula I or a salt thereof.

DETAILED DESCRIPTION

Figure 1A:
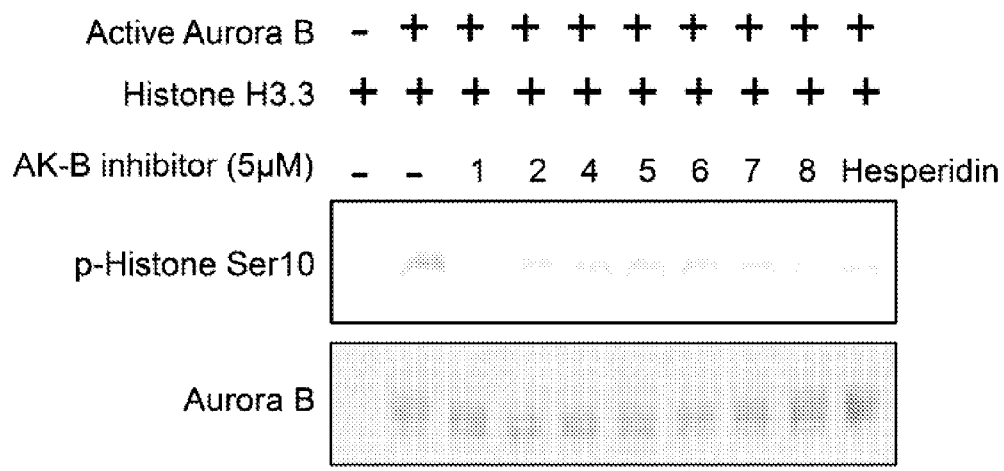
FIG. 1. (A) Compounds 1-8 inhibit Aurora B kinase activity in vitro. An inactive histone 3.3 protein was used as the substrate for an in vitro kinase assay with active Aurora B and 100 μmol/L ATP. Proteins were resolved by Western blotting. (B) Shows the percent of Aurora B remaining kinase activity.

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

As used herein, "animal" includes a mammal such as for example, a human.

As used herein "pathological condition associated with Aurora B kinase" includes, cancer.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; and $(C_2-C_6)$alkanoyloxy can be acetoxy, propanoyloxy, butanoyloxy, isobutanoyloxy, pentanoyloxy, or hexanoyloxy.

A specific compound of formula I is a compound of formula Ia:

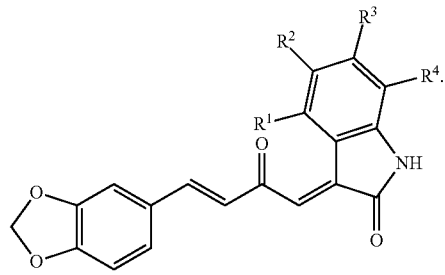

A specific value for ring A is substituted with one or more $(C_1-C_6)$alkoxy.

A specific value for ring A is 3,4,5-trihydroxyphenyl or 4-nitrophenyl.

A specific compound is a compound wherein at least one of $R^1$, $R^2$, $R^3$, and $R^4$ is other than H.

A specific compound is a compound wherein at least one of $R^1$, $R^2$, $R^3$, and $R^4$ is halo, cyano, nitro, $(C_3-C_6)$cycloalkyl, $(C_1-C_6)$alkoxy, $(C_1-C_6)$alkanoyl, $(C_1-C_6)$alkoxycarbonyl, or $(C_2-C_6)$alkanoyloxy.

A specific compound is a compound wherein at least one of $R^1$, $R^2$, $R^3$, and $R^4$ is halo.

A specific compound is a compound wherein at least one of $R^1$, $R^2$, $R^3$, and $R^4$ is fluoro or chloro.

A specific compound is a compound wherein $R^1$, $R^2$, $R^3$, and $R^4$ are each H.

A specific value for $R^2$ is halo.
A specific value for $R^2$ is fluoro or chloro.
A specific value for $R^3$ is halo.
A specific value for $R^3$ is fluoro or chloro.

Processes for preparing compounds of formula I are provided as further embodiments of the invention and are illustrated in Scheme 1 in which the meanings of the generic radicals are as given above unless otherwise qualified.

Scheme 1:

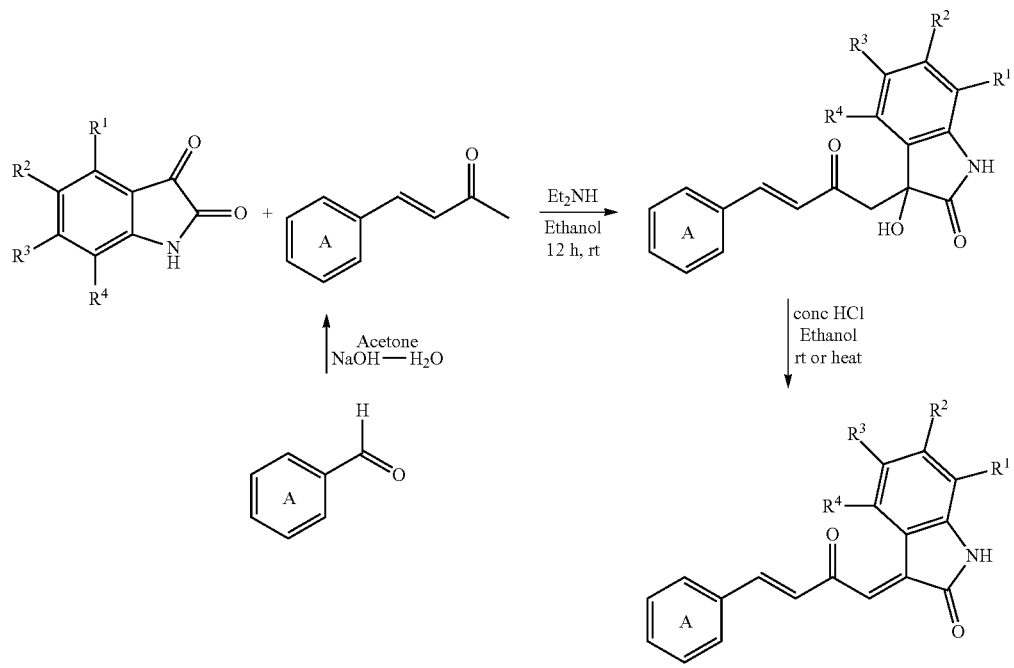

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to inhibit Aurora B kinase or to treat cancer may be determined using pharmacological models which are well known to the art, or using the assays described in the Examples below.

The invention will now be illustrated by the following non-limiting Examples.

EXAMPLES

Example 1

Preparation of Compound 1

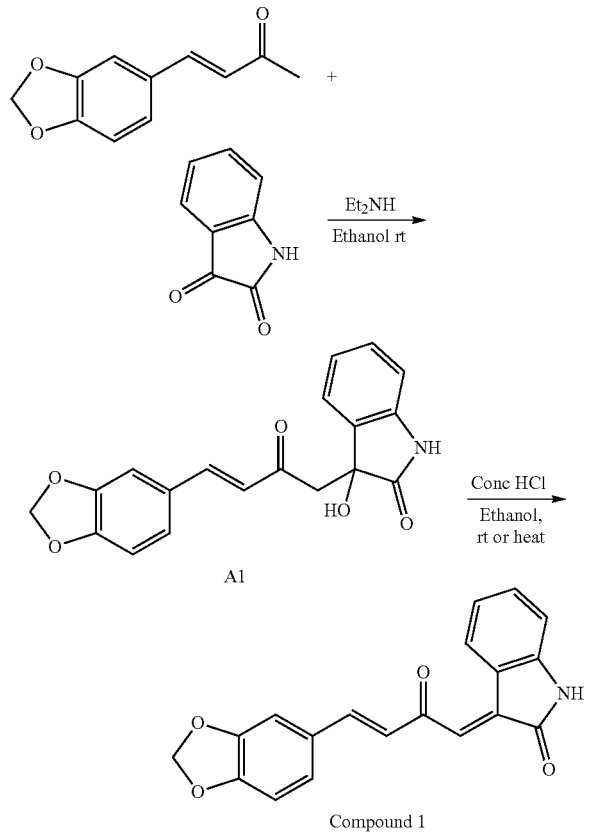

To a stirred solution of isatin (10 mmol) and diethylamine (0.3 mmol) in ethanol was added 3,4-(Methylenedioxy)benzylideneacetone (10 mmol). The resulting mixture was stirred at room temperature for 12 h. The solid separated out was filtered and washed with ether and ethyl acetate. The obtained yellow solid was recrystallized from ethanol to give 2.8 g of A1. 1H NMR (400 MHz, $d_6$-DMSO): 10.21 (s, 1H), 7.45 (d, 1H, J=16.05), 7.30 (s, 1H), 7.25 (d, 1H, J=7.44 Hz), 7.13-7.18 (m, 2H), 6.95 (d, 1H, J=8.04 Hz), 6.87 (t, 1H, J=7.44 Hz), 6.75 (d, 1H, J=7.64 Hz), 6.61 (d, 1H, J=16.24 Hz), 6.07 (s, 2H), 6.01 (s, 1H), 3.60 (d, 1H, J=16.44 Hz), 3.18 (d, 1H, J=16.44 Hz).

To a stirred suspension of A1 (0.5 g) in ethanol (15 mL) was added 37% HCl (5 mL). The reaction mixture was stirred at room temperature for 7 days or heat at 80° C. for 30 min. After this time, the obtained red solid (compound 1) was filtered and purified by recrystallization from ethanol. 1H NMR (400 MHz, $d_6$-DMSO): 10.74 (s, 1H), 8.35 (d, 1H, J=7.64 Hz), 7.70 (d, 1H, J=16.05 Hz), 7.49 (d, 1H, J=1.37 Hz), 7.31-7.37 (m, 3H), 7.25 (s, 1H), 6.95-7.02 (m, 2H), 6.87 (d, 1H, J=7.83 Hz), 6.11 (s, 2H).

Example 2

Preparation of Compound 4

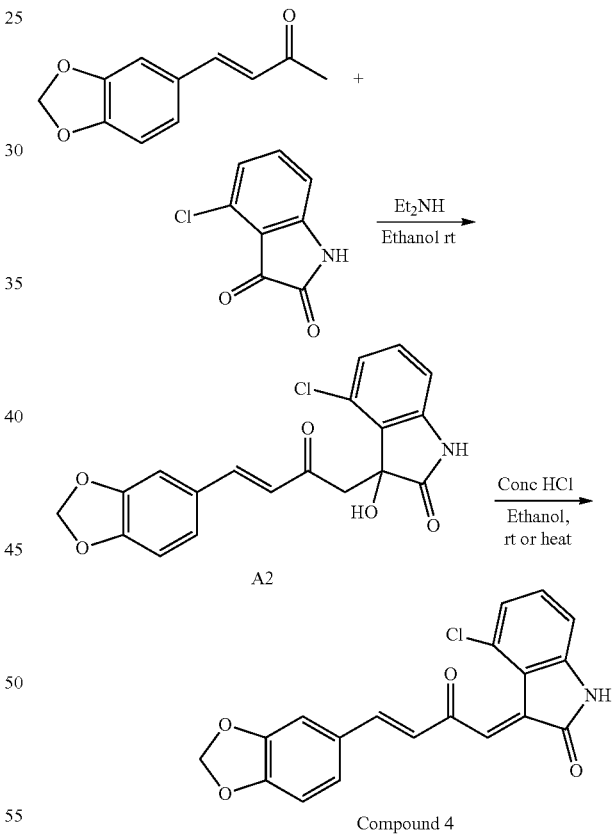

Compound 4 was prepared according to the method described in Example 1 using 4-Chloroisatin (10 mmol) and 3,4-(Methylenedioxy)benzylideneacetone (10 mmol).

Compound A2: 1H NMR (400 MHz, $d_6$-DMSO): 10.47 (s, 1H), 7.49 (d, 1H, J=16.24 Hz), 7.33 (s, 1H), 7.17 (m, 2H), 6.95 (d, 1H, J=8.02 Hz), 6.84 (d, 1H, J=8.22 Hz), 6.75 (d, 1H, J=7.63 Hz), 6.63 (d, 1H, J=16.24 Hz), 6.18 (s, 1H), 6.07 (s, 2H), 3.98 (d, 1H, J=17.02 Hz), 3.30 (d, 1H, J=17.02 Hz).

Compound 4: MS (ESI): Calculated: 353.0455 Obtained: 354.0047 (M+1) 355.0081 (M+2) 356.0019 (M+3).

Example 3

Preparation of Compound 5

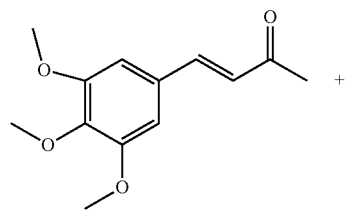

+

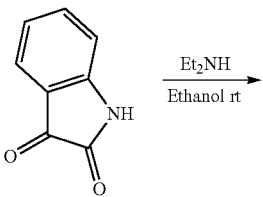

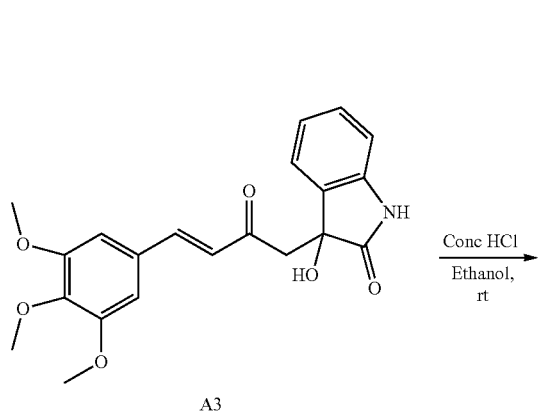

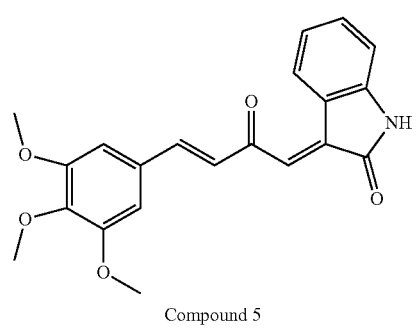

Compound 5

To a stirred solution of isatin (10 mmol) and diethylamine (0.3 mmol) in ethanol was added 3,4,5-trimethoxybenzylideneacetone (10 mmol). The resulting mixture was stirred at room temperature for 12 h. After this time, the solution was evaporated and purified by column chromatography to give A3. 1H NMR (400 MHz, $d_6$-DMSO): 10.22 (s, 1H), 7.50 (d, 1H, J=16.25), 7.26 (d, 1H, J=7.44 Hz), 7.15 (t, 1H, J=7.63 Hz), 7.01 (s, 2H), 6.88 (t, 1H, J=7.43 Hz), 6.71-6.79 (m, 2H), 6.03 (s, 1H), 3.80 (s, 6H), 3.68 (s, 3H), 3.63 (d, 1H, J=16.24 Hz), 3.18 (d, 1H, J=16.44 Hz).

To a stirred solution of A3 (50 mg) in ethanol (2 mL) was added 37% HCl (0.5 mL). The reaction mixture was stirred at room temperature for 3 h. After this period, the obtained red solid was filtered and purified by recrystallization from ethanol to provide Compound 5. MS (ESI): Calculated: 365.1263; Obtained: 366.0841 (M+1).

Example 4

Preparation of Compound 7

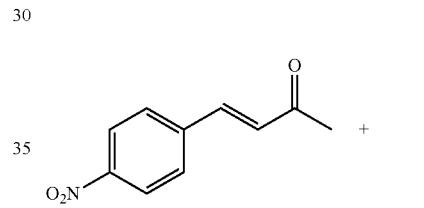

+

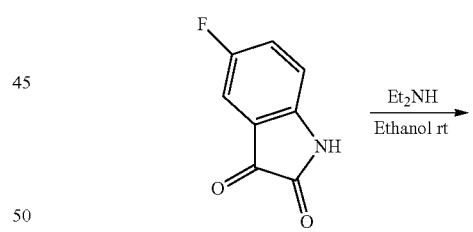

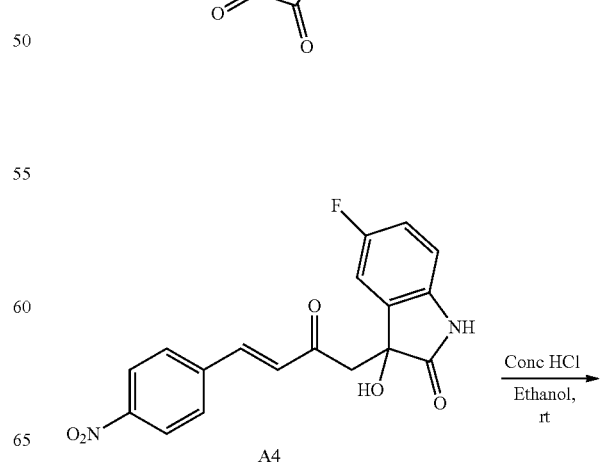

13
-continued

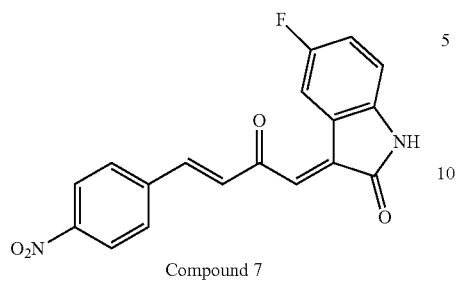

Compound 7

Compound 7 was prepared according to the method described in Example 1 using 5-fluoroisatin (10 mmol) and 4-Nitrobenzylidineacetone (10 mmol).

Compound A4: 1H NMR (400 MHz, $d_6$-DMSO): 10.29 (s, 1H), 8.25 (d, 2H, J=8.42 Hz), 7.94 (d, 2H, J=8.61 Hz) 7.65 (d, 1H, J=16.44), 7.20 (dd, 1H), 6.90-7.02 (m, 2H), 6.75 (m, 1H), 6.21 (s, 1H), 3.72 (d, 1H, J=16.83 Hz), 3.30 (d, 1H, J=16.83 Hz).

Compound 7: MS (ESI): Calculated: 338.0703 Obtained: 339.0292 (M+1).

Example 5

Preparation of Compound 8

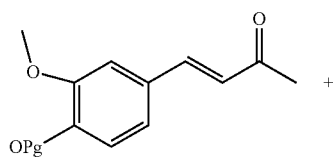

+

14
-continued

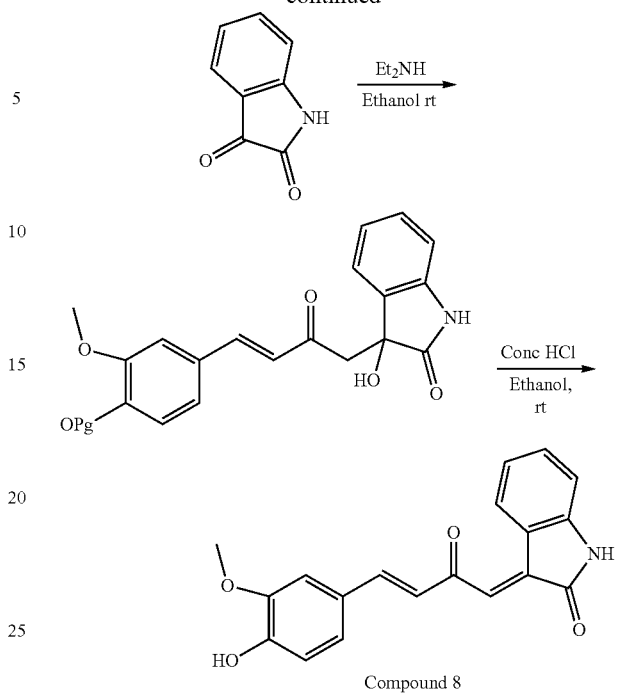

Compound 8

Pg = H or Protecting group (THP)

Compound 8 was prepared according to the method described in Example 1 using isatin (2 mmol) and 3-methoxy-4-tetrahydropyranoxy benzylidineacetone (or Vanillylidenacetone) (2 mmol). MS (ESI): Calculated: 321.1001; Obtained: 322.0638 (M+1).

Using procedures similar to those described herein the following compounds 2, 3, and 6 were also prepared. Compounds 1-8 shown in Table 1 as well as salts thereof, are compounds of the invention.

TABLE 1

| S. No. | Structure | MS (ESI) |
|---|---|---|
| 1 | 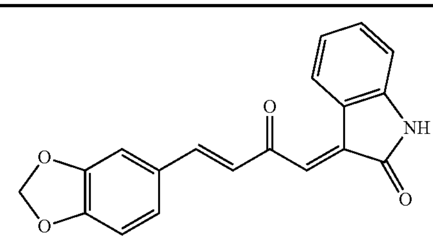 | Calculated: 319.0845; Obtained: 320.0902 (M + 1) |
| 2 | 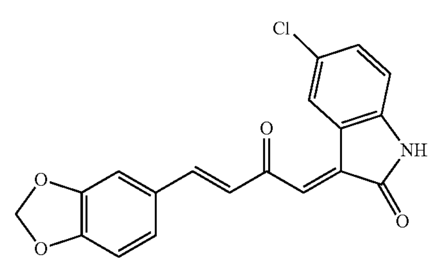 [SMILES: O=C(/C=C/c1ccc2c(c1)OCO2)/C=C1/C(=O)Nc2ccc(Cl)cc21] | Calculated: 353.0455 Obtained: 354.0524 (M + 1) 355.0558 (M + 2); 356.0497 (M + 3) |

TABLE 1-continued

| S. No. | Structure | MS (ESI) |
|---|---|---|
| 3 | 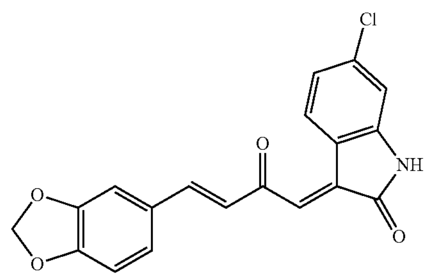 [SMILES: O=C(/C=C/c1ccc2c(c1)OCO2)/C=C1/C(=O)Nc2cc(Cl)ccc21] | Calculated: 353.0455<br>Obtained: 354.0530 (M + 1)<br>355.0547 (M + 2); 356.0485 (M + 3) |
| 4 | 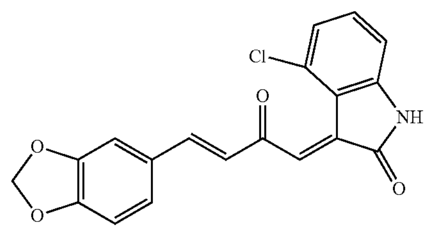 [SMILES: O=C(/C=C/c1ccc2c(c1)OCO2)/C=C1/C(=O)Nc2cccc(Cl)c21] | Calculated: 353.0455;<br>Obtained: 354.0047 (M + 1),<br>355.0081 (M + 2), and 356.0019 (M + 3) |
| 5 | 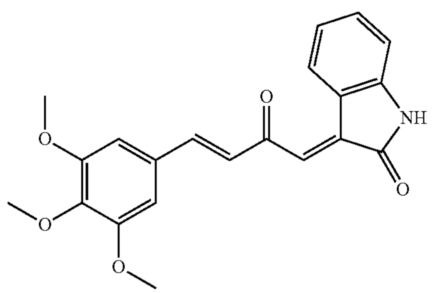 [SMILES: COc1cc(/C=C/C(=O)/C=C2/C(=O)Nc3ccccc32)cc(OC)c1OC] | Calculated: 365.1263;<br>Obtained: 366.0841 (M + 1) |
| 6 | 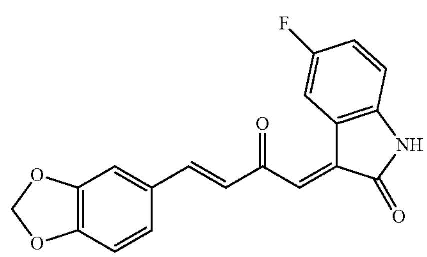 [SMILES: O=C(/C=C/c1ccc2c(c1)OCO2)/C=C1/C(=O)Nc2ccc(F)cc21] | Calculated: 337.0750<br>Obtained: 338.0819 (M + 1) |
| 7 | 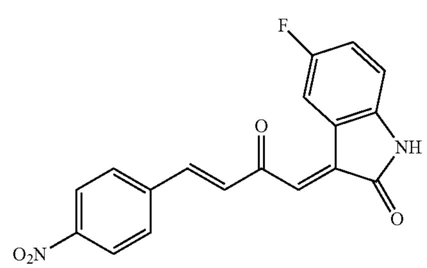 [SMILES: O=C(/C=C/c1ccc([N+](=O)[O-])cc1)/C=C1/C(=O)Nc2ccc(F)cc21] | Calculated: 338.0703;<br>Obtained: 339.0292 (M + 1) |
| 8 | 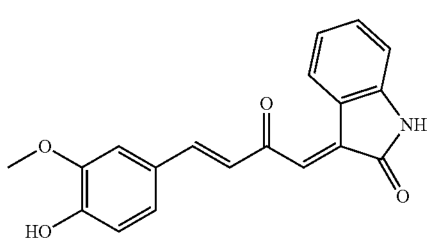 [SMILES: COc1cc(/C=C/C(=O)/C=C2/C(=O)Nc3ccccc32)ccc1O] | Calculated: 321.1001;<br>Obtained: 322.0638 (M + 1). |

The biological activity of representative compounds of the invention can be evaluated using known assays or using the assays described in Example 6.

Example 6

Biological Assays

Reagents and Materials

All cell lines were purchased from American Type Culture Collection (ATCC) and were cultured in monolayers at 37° C. in a 5% $CO_2$ incubator according to ATCC protocols. Cells were cytogenetically tested and authenticated before the cells were frozen. Each vial of frozen cells was thawed and maintained for about two months (10 passages). For transfection experiments, the jetPEI (Qbiogene, Inc., Montreal, Canada) transfection reagent was used following the manufacturer's instructions.

Anchorage-Independent Cell Transformation Assay

Tumor cells are suspended in basal medium Eagle (BME) medium and added to 0.6% agar, with different concentrations of Compound 1 in a base layer and a top layer of 0.3% agar. The cultures are maintained at 37° C. in a 5% $CO_2$ incubator for 1 to 2 weeks and then colonies are counted under a microscope using the Image-Pro Plus software (v.4) program (Media Cybernetics, Silver Spring, Md.).

Cell Cycle and Apoptosis Analyses

Cells are plated in 60-mm plates and treated or not treated with Compound 1 for the indicated time. At each time point, cells are fixed in 70% ethanol and stored at −20° C. for 24 h. After staining, the cell cycle distribution or apoptosis is determined using a BD FACSCalibur Flow Cytometer (BD Biosciences, San Jose, Calif.).

MTS Assay

To estimate the cytotoxicity of Compound 1, cells are seeded ($8\times10^3$ cells per well) in 96-well plates and cultured overnight. Cells are fed with fresh medium and treated with different doses of Compound 1. After culturing for various times, the cytotoxicity of Compound 1 is measured using an MTS assay kit (Promega, Madison, Wis.) according to the manufacturer's instructions.

Western Blot Analysis

Proteins are resolved by SDS-PAGE and transferred onto polyvinylidene difluoride membranes (Millipore, Mass.), which are blocked with nonfat milk and hybridized with specific primary antibodies. The protein bands are visualized using an enhanced chemiluminescence reagent (GE Healthcare, Pittsburgh, Pa.) after hybridization with a horseradish peroxidase-conjugated secondary antibody.

Aurora B and Aurora A In vitro Kinase Assay

Inactive histone 3 proteins (1 µg) are used as the substrate for an in vitro kinase assay with 100 ng of active Aurora B or Aurora A kinase. Reactions are carried out in 1×kinase buffer (25 mM Tris-HCl pH 7.5, 5 mM beta-glycerophosphate, 2 mM dithiothreitol (DTT), 0.1 mM $Na_3VO_4$, 10 mM $MgCl_2$ and 5 mM $MnCl_2$) containing 100 µM ATP at 30° C. for 30 minutes. Reactions are stopped and proteins detected by Western blotting.

Immunofluorescence Microscopy

A549 cells are seeded in four-chamber slides and cultured overnight. The cells are then treated with DMSO or Compound 1 (1 µM) for 48 h at 37° C. After treatment, the cells are washed with PBS and fixed with methanol for 12 hours, followed by blocking with 3% PBS for 1 hour. The cells are then incubated with α-tubulin antibodies (1:100) overnight and DNA is stained with 4'-6-diamidino-2-phenylindole (DAPI, Pierce) for 30 minutes at room temperature. The cells are evaluated by fluorescent microscopy.

Hematoxylin-Eosin Staining and Immunohistochemistry

Tumor tissues from mice are embedded in a paraffin block and subjected to hematoxylin and eosin (H&E) staining and immunohistochemistry. Tumor tissues are deparaffinized and hydrated, then permeabilized with 0.5% Triton X-100/l PBS for 10 min, hybridized with Ki-67 (1:500) as the primary antibody and an HRP-conjugated goat anti-rabbit or mouse IgG antibody is used as the secondary antibody. After developing with 3,30-diaminobenzidine, the sections are counterstained with H&E. All sections are observed by microscope and the Image-Pro Plus software (v.4) program (Media Cybernetics).

Statistical Analysis

All quantitative data are expressed as mean values±S.D. or S.E. and significant differences are determined by Student's t test or by one-way ANOVA. A probability value of $P<0.05$ is used as the criterion for statistical significance.

Results

The Predicted Binding Mode of Compound 1 with Aurora B and Cytotoxicity

A molecular docking analysis was performed using Glide v5.7 to screen a compound library against the structure of Aurora B. Compound 1 was identified as a potential Aurora B inhibitor based on its high docking score. The predicted binding mode of Compound 1 and Aurora B showed that Compound 1 occupies the ATP-binding site and forms a hydrogen bond with amino acid Ala173 in the hinge linker region, which is quite similar to the binding of other Aurora B kinase inhibitors. The toxicity of Compound 1 on both MRC-5 normal lung cells and A549 lung cancer cells was then examined. The result showed that Compound 1 possessed substantial toxicity to both cell types at concentrations greater than 10 µM. At a concentration of 1 µM or less, no obvious cytotoxic effects were observed in either cell line. At 5 µM, Compound 1 treatment for 48 hours resulted in a weak toxicity toward A549 cancer cells, but not to MRC-5 normal cells.

Compound 1 Inhibits Anchorage-Independent Growth of Human Lung Cancer Cells

The effect of Compound 1 treatment on anchorage-independent growth of human lung cancer cells, including A549, H1650, and H520 cells was then examined. Treatment of these cells with Compound 1 potently inhibited the anchorage-independent growth in a concentration-dependent manner. Compound 1 at 0.5 or 1 µM caused a decrease of more than 80% or 90% compared to control in all cell lines detected. The inhibition by Compound 1 was not due to cytotoxicity because no toxicity was observed at 1 µM Compound 1. Therefore, the results indicated that Compound 1 is a very potent compound possessing anti-tumor activity.

The effect of compound 1 in a pair of colon cancer cell lines, p53 wildtype (HCT116 $p53^{+/+}$) and p53-deficient (HCT116 $p53^{-/-}$) cells was also examined to determine whether the sensitivity of cells to compound 1 directly correlates with the status of p53 in cells. Soft agar assay results showed that HCT116 $p53^{-/-}$ cells are more sensitive to compound 1 than HCT116 $p53^{+/+}$ cells. Compound 1 at 0.05 µM caused a 40% inhibition of growth of HCT116 $p53^{-/-}$ cells, whereas no inhibition was observed in the wildtype p53 cells. Moreover, 0.1 µM compound 1 inhibited growth by more than 95% in HCT116 $p53^{-/-}$ cells but only 55% inhibition in HCT116 $p53^{+/+}$ cells. These data are consistent with another report showing that $p53^{-/-}$ cells are more sensitive to Aurora B inhibitors than $p53^{+/+}$ cells.

Compound 1 is a Potent Inhibitor of Aurora B, but not Aurora A

An in vitro kinase assay was used to determine whether Compound 1 could inhibit Aurora B kinase activity using recombinant Aurora B protein and various concentrations of Compound 1. Results indicated that the phosphorylation of histone H3 on Ser10, an Aurora B substrate, was strongly inhibited by Compound 1 in a concentration-dependent manner. For example, 0.05 µM Compound 1 caused a 22% inhibition of Aurora B kinase activity and 0.1 µM Compound 1 resulted in a 50% inhibition. At a concentration of 1 µM, only a weak histone H (Ser10) band was observed. The effect of Compound 1 on Aurora A kinase activity using an in vitro kinase assay was also examined. No effect on histone H3 (Ser10) phosphorylation was observed at 1 µM Compound 1 compared with control. These results also demonstrate that compound 1 is a potent inhibitor of Aurora B kinase.

Compound 1 Blocks Phosphorylation of Histone H3 on Ser10 in Lung Cancer Cells

The effect of compound 1 on Aurora B downstream signaling was also evaluated to demonstrate that compound 1 is acting through inhibition of Aurora B in cancer cells. Evidence indicated that histone H3 is a direct downstream target of the Aurora kinases. Phosphorylation of a highly conserved serine residue (Ser10) in histone H3 is thought to be crucial for entry into mitosis. Compound 1 suppressed histone H3 phosphorylation on Ser10 in cancer cells in a dose- and time-dependent manner, suggesting that the Aurora B kinases are involved in the antitumor activity of Compound 1.

Compound 1 Induces Polyploidy, Cell Cycle Arrest, and Apoptosis in Lung Cancer Cells Aurora B inhibition leads to failure in cytokinesis and abnormal exit from mitosis, which could result in polyploidy cells, cell cycle arrest, and ultimately apoptosis. The ability to induce polyploidy cells was further examined in A549 cells treated or not treated with Compound 1. Immunofluorescence results showed that treatment of A549 cells with 1 µM Compound 1 caused the induction of polyploidy cells, whereas no polyploidy cells were observed in control cells. In addition, Compound 1 treatment for 48 hours caused an increase in the number of A549 and H520 cells occupying the G2/M phase. Moreover, exposure of these cells to Compound 1 for 72 hours induced apoptosis as measured by Annexin V/PI staining. For example, exposure to 5 µM Compound 1 induced 48% or 82% apoptosis in A549 cells and H520 cells, compared to 8% or 38% in untreated control cells, respectively. These results demonstrate that compound 1, as an Aurora B inhibitor, induces polyploidy, apoptosis and G2/M phase arrest in cancer cells and thus inhibits the growth of cancer cells.

Knockdown of Aurora B Decreases the Sensitivity of Cancer Cells to Compound 1

The effect of knocking down Aurora B expression in A549 cancer cells on the cell's sensitivity to Compound 1 was evaluated. The efficiency of shRNA knockdown was examined and the expression of Aurora B was obviously decreased after shRNA transfection. Moreover, the growth of cells in soft agar also decreased after transfection compared with the mock group. Compound 1 (0.5 µM) inhibited anchorage-independent growth of A549 cells transfected with mock shRNA by about 90%. In contrast, the inhibition was less than 40% in A549 cells transfected with Aurora B shRNA, indicating that A549 cells transfected with Aurora B shRNA were more resistant to Compound 1 treatment. These results suggested that Aurora B plays an important role in the sensitivity of A549 cells to the anti-proliferative effects of Compound 1.

Kinase Profile Result

A kinase profile assay was performed by Millipore, to examine other potential targets of Compound 1. Only Akt2 activity was suppressed more than 50% after 5 µM compound 1 treatment, compared with the control (Table 2). In addition, the kinase activity of Aurora A was decreased less than 25% at 5 µM Compound 1.

TABLE 2

| Kinase | HOI-07 (5 µM) |
|---|---|
| Abl | 109 |
| AMPK-alpha1 | 96 |
| AMPK-alpha2 | 90 |
| Aurora A | 76 |
| CDK1/cyclinB | 86 |
| CDK2/cyclinA | 98 |
| CDK3/cyclinE | 99 |
| CHK2 | 75 |
| c-Kit | 123 |
| CSK | 110 |
| c-RAF | 87 |
| c-Src | 99 |
| DYRK2 | 97 |
| EGFR | 106 |
| EGFR (T790M, L858R) | 101 |
| FAK | 104 |
| FGFR1 | 86 |
| Flt3 | 92 |
| Fyn | 99 |
| GSK3 alpha | 85 |
| GSK3 beta | 94 |
| IGF-1R | 105 |
| IKK alpha | 83 |
| IKK beta | 68 |
| JNK1 alpha1 | 104 |
| JNK2 alpha2 | 89 |
| KDR | 93 |
| LKB1 | 87 |
| MAPK1 | 100 |
| MAPK2 | 102 |
| MEK1 | 104 |
| Met | 89 |
| MKK4 | 130 |
| MKK6 | 129 |
| MKK7 beta | 94 |
| MSK1 | 98 |
| MSK2 | 79 |
| mTOR | 136 |
| mTOR/FKBP12 | 86 |
| p70S6K | 72 |
| PDK1 | 96 |
| Pim-1 | 96 |
| PKB alpha (Akt1) | 68 |
| PKB beta (Akt2) | 47 |
| RSK2 | 94 |
| PI3-K alpha | 102 |
| PI3-K beta | 103 |
| PI3-K gamma | 100 |
| PI3-K delta | 105 |

Compound 1 Inhibits Akt1 and 2 Kinase Activities In Vitro, but not in Ex Vivo

According to the kinase profiler assay results, Akt2 also might be a potential target of Compound 1. An Akt1 and Akt2 in vitro kinase assays was performed. The results indicated that Compound 1 inhibited both Akt1 and Akt2 in vitro kinase activities in a concentration-dependent manner. Treatment with 5 µM Compound 1 caused a 32% or 52% inhibition of Akt1 or Akt2 activity, respectively, which is quite consistent with the kinase profiler assay result. However, Western blot analysis of A549 cells and H520 cells treated with Compound 1 showed that Compound 1 treatment has no effect on the phosphorylation of Akt or its downstream signaling molecules, including Akt (Ser473), GSK3β (Ser9), p70S6K (Thr389) and S6 (Ser235,236). These results indicated that although Compound 1 can inhibit Akt1 and Akt2 in vitro kinase activity, it has no effect on Akt activity in cancer cells, suggesting that Akt1 and Akt2 might not be the major antitumor targets of Compound 1.

Compound 1 Suppresses the Growth of A549 Xenografts In vivo

The ability of Compound 1 to inhibit the growth of human A549 lung cancer cell xenografts in athymic nude mice was then evaluated. Tumor volumes were measured twice a week and mouse weights were determined once a week. Compound 1 caused a marked reduction in tumor size in the human A549 xenograft model. In mice treated with Compound 1 at 20 mg/kg, twice a week intraperitoneally, mean tumor volumes were reduced to 164 mm$^3$ in comparison with control group (408 mm$^3$) (P<0.01). In addition, no obvious loss of body weight was observed, indicating that Compound 1 is well tolerated by the mice. Moreover, the effects of Compound 1 on a tumor proliferation marker were evaluated by immunohistochemistry and H&E staining of A549 tumor tissues after the 31 days of treatment. The expression of Ki-67 was markedly decreased by Compound 1. These results indicated that Compound 1 suppressed tumor growth in vivo.

Discussion

Cancer is a disease that is characterized by uncontrolled proliferation of abnormal cells. Modulation of atypical cell cycle regulation would therefore be a valuable therapeutic strategy for different types of tumors. Aurora kinases regulate many processes during cell division. Aurora B kinases are essential for chromosome condensation, kinetochore function, cytokinesis and the proper function of the spindle-assembly checkpoint when spindle tension is perturbed (Carmena, M. and W. C. Earnshaw, Nat Rev Mol Cell Biol, 2003. 4 (11): p. 842-54; Kallio, M. J., et al., Curr Biol, 2002. 12 (11): p. 900-5; Ditchfield, C., et al., J Cell Biol, 2003. 161 (2): p. 267-80; and Yang, H., et al., FEBS Lett, 2005. 579 (16): p. 3385-91). Accumulating evidence has shown that Aurora B is implicated in cancer. For example, the expression of Aurora B is frequently elevated in various types of cancer, including NSCLC, colon, prostate (Tatsuka, M., et al., Cancer Res, 1998. 58 (21): p. 4811-6; Vischioni, B., et al., Mol Cancer Ther, 2006. 5 (11): p. 2905-13; and Chieffi, P., et al., Prostate, 2006. 66 (3): p. 326-33). The evidence linking Aurora overexpression and malignancy has generated significant interest in the development of small molecule inhibitors.

Oxindoles (indolin-2-ones) are an important class of molecules, which are known to possess a wide variety of biological properties, and in particular, as protein kinase inhibitors (Millemaggi A, T. R., European Journal of Organic Chemistry, 2010 (24): p. 4527-4547). In the present study, Compound 1 was identified using molecular docking methods as an Aurora B kinase inhibitor.

The results of an Aurora B kinase assay showed that Compound 1 potently and dose-dependently inhibited Aurora B kinase in vitro activity, indicating that this compound is a potent and novel Aurora B inhibitor. In addition, Compound 1 had no effect on Aurora A kinase in vitro activity at the same concentration. A previous report showed that cells treated with an Aurora kinase inhibitor entered and exited mitosis without cell division, and then proceeded to a second S phase. Therefore, the activity of Compound 1 on cancer cells was examined. Results showed that Compound 1 suppressed cell growth in a panel of NSCLC cell lines, associated with induction of polyploidy cells, accumulation of $G_2$/M cells, as well as apoptosis, which is consistent with Aurora B inhibition. Moreover, knocking down Aurora B expression in A549 cells decreased their sensitivity to Compound 1, indicating that Aurora B plays an important role in the antitumor activity of Compound 1. An in vivo xenograft study also indicated that Compound 1 effectively suppressed tumor growth without affecting mouse body weight and was accompanied with a decrease in Ki-67 expression, which is a marker of proliferation.

According to kinase profiling results, in which 49 kinases treated or not treated with Compound 1, Akt might also be a potential target of Compound 1. Further experimental results showed that Compound 1 inhibited Akt1 and Akt2 kinase activity in vitro at a higher concentration (1 µM or more) than that required for Aurora B inhibition (1 µM or lower). However, it had no effect on Akt downstream signaling in cancer cells, indicating that Akt might not be a major target of Compound 1. Together, these results indicated that Compound 1 is a potent and selective inhibitor of Aurora B.

Example 7

Xenograft Mouse Model

Figure 1B:
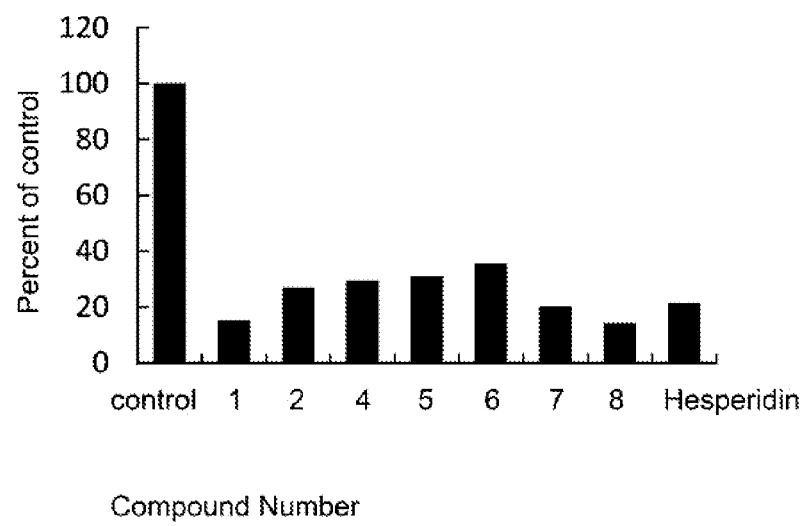
Figure 2:
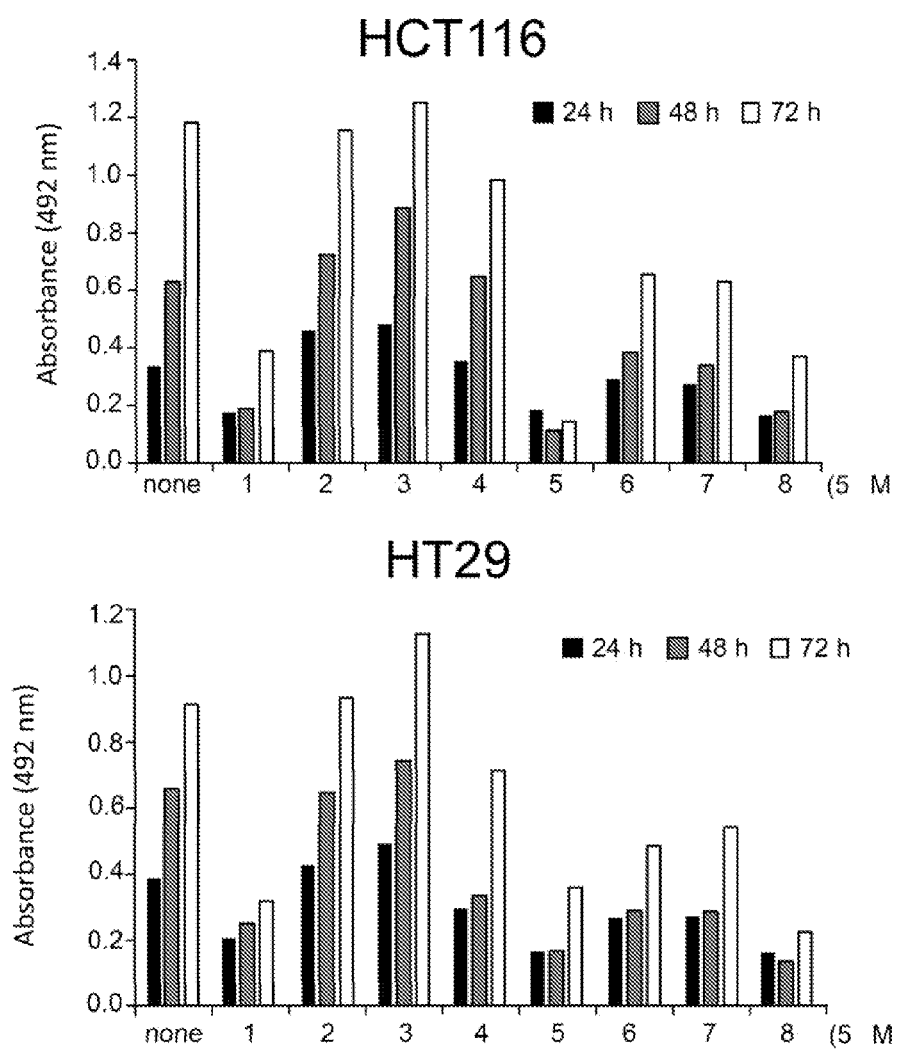
FIG. 2. Compounds 1-8 decrease viability of HCT116 (upper panel) and HT29 (lower panel) colon cancer cells. At 5 μM, each of the compounds causes a significant decrease in viability of colon cancer cells.
Figure 3A:
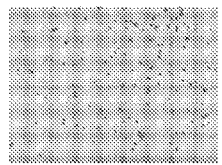
FIGS. 3A and 3B. Compounds 1-8 suppress the anchorage-independent growth of HCT116 cells. The asterisk indicates a significant (*p<0.05, **p<0.01) decrease in colony formation in cells treated with each compound compared with the DMSO treated control group. Two concentrations of each compound, 0.5 μM and 5 μM were tested. At 0.5 μM compounds 1, 5, 6 and 8 showed the best efficiency, followed by compounds 3 and 7. Compounds 2 and 4 had no effect. At 5 μM, all the compounds were highly effective to inhibit anchorage-independent growth.
Figure 3A:
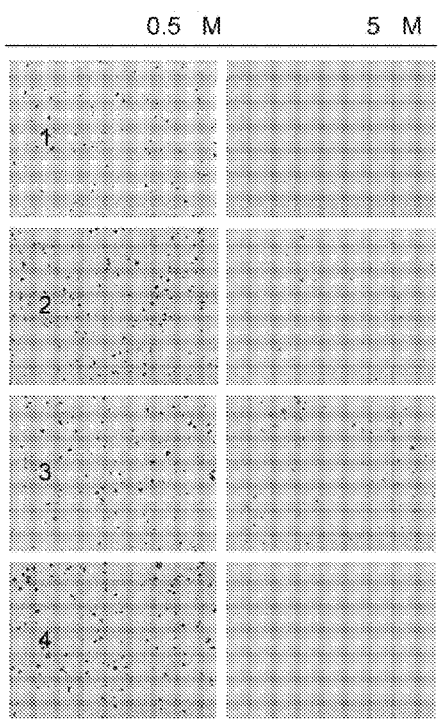
Figure 3A:
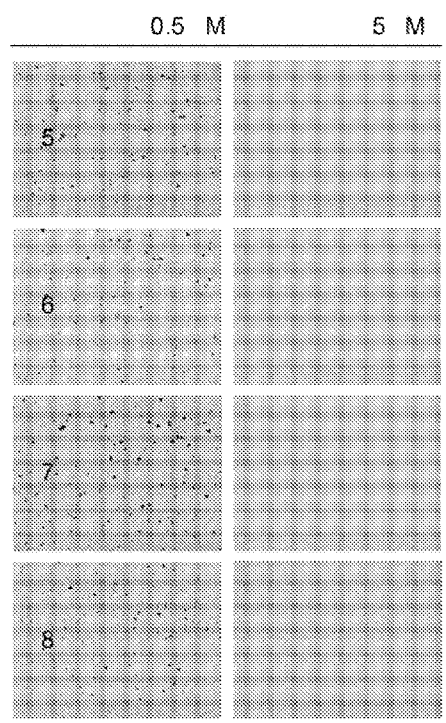
Figure 3B:
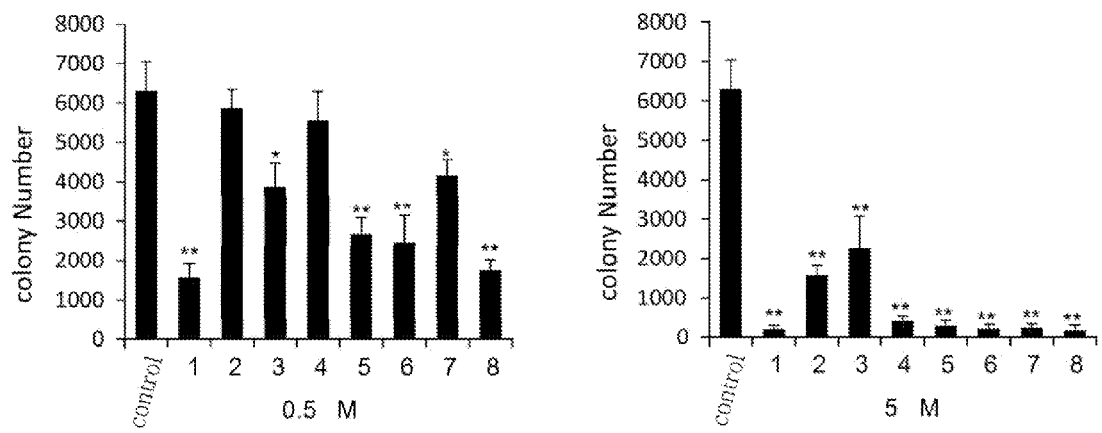
Figure 4A:
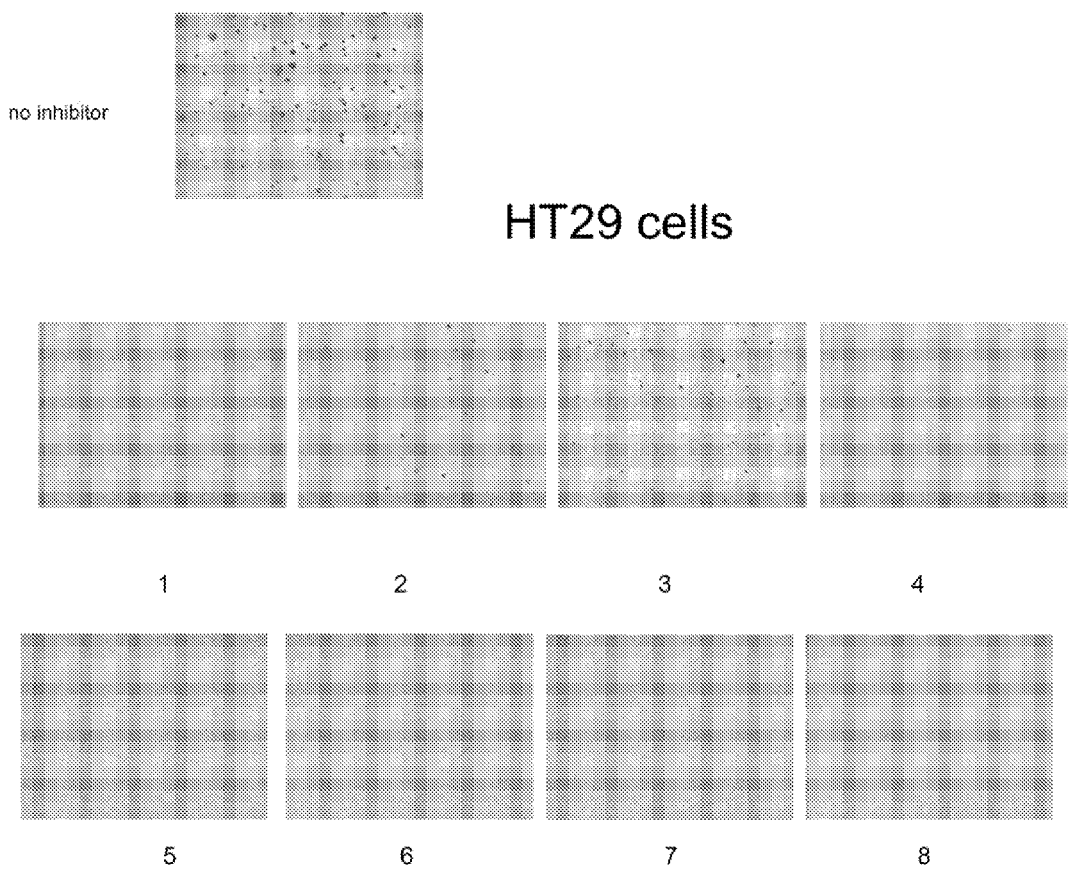
FIGS. 4A and 4B. Compounds 1-8 suppress the anchorage-independent growth of HT29 colon cancer cells at a concentration of 5 μM. The asterisk indicates a significant (**p<0.01) decrease in colony formation in cells treated with each compound compared with the DMSO-treated group.
Figure 4B:
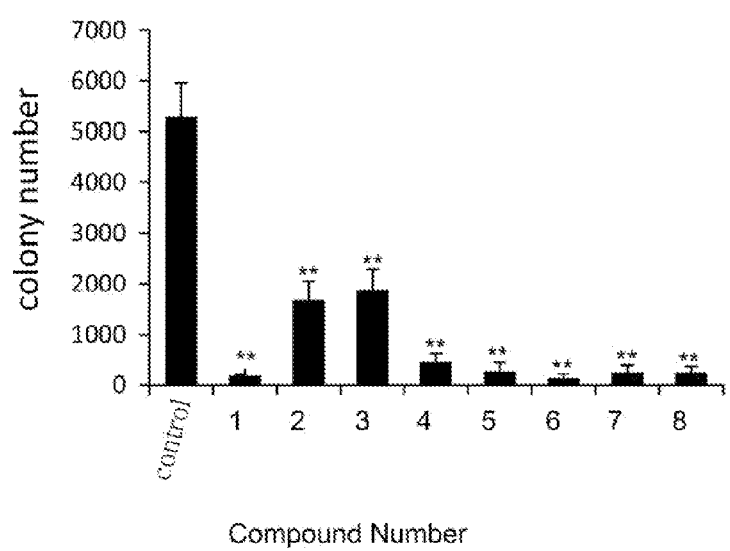
Figure 5:
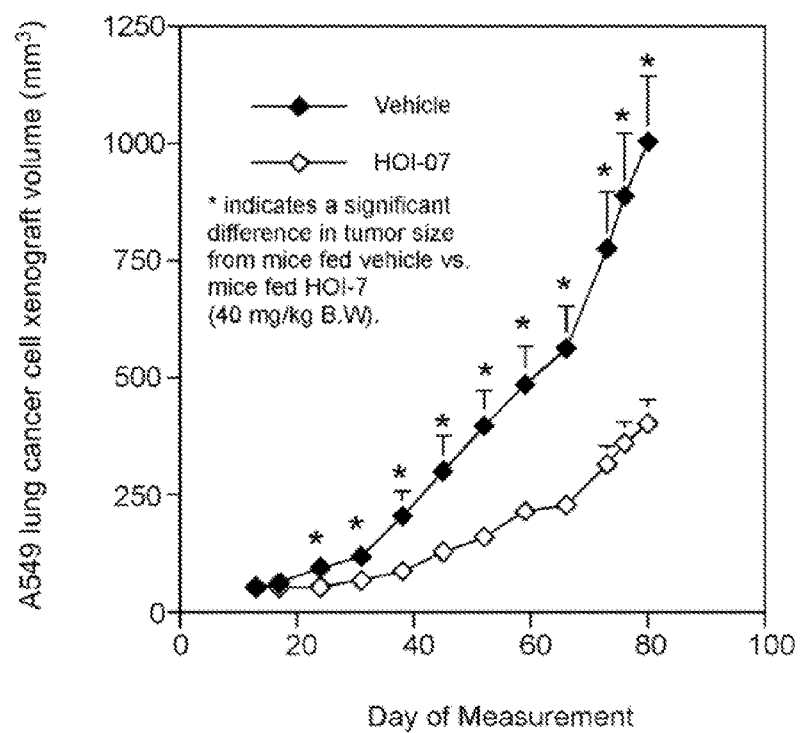
FIG. 5. Illustrates Xenograph data from Example 5 for Compound 1.

Athymic nude mice (6 week old nu/nu female mice, Harlan Laboratory, Minneapolis, Minn.) were inoculated in the right flank with A549 lung cancer cells (3*10$^6$ cells/mouse). Mice were maintained under "specific pathogen-free" conditions based on the guidelines established by the University of Minnesota Institutional Animal Care and Use Committee. Tumors were allowed to grow to an average of ~53.5±34.5 mm$^3$ and then mice were divided into 2 equal groups with a similar average tumor volume (group 1; n=15), vehicle only; (group 2, n=20), compound 1 at 40 mg/kg. Treatment with vehicle or compound 1 was initiated on Day 13 after inoculation of cells and continued to Day 80 (~9 wks) and was administered by oral gavage 5 times a week. Tumor volume was measured once a week and body weight was measured once a week. Compound 1 was prepared in 2.5% DMSO/5% PEG 400/5% Tween-80 in 1×PBS and sonicated for ~20 minutes. The final tumors from the vehicle-treated group were significantly larger in volume (1004±140.1) than the Compound 1 treated group (403.2±50.0). Data are shown as means±S.E (FIG. 1). No toxicity was observed in any mice. Oral administration of Compound 1 was highly effective in preventing xenograft growth of A549 lung cancer cells.

Example 8

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

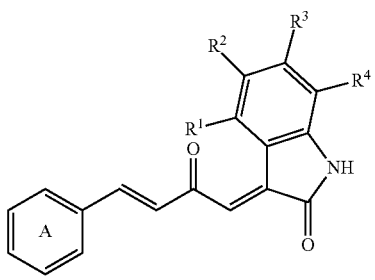

(I)

wherein:
ring A is substituted with one or more groups independently selected from hydroxy, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo;

$R^1$ is H, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo; or $R^1$ and $R^2$ taken together are methylenedioxy or ethylenedioxy;

$R^2$ is H, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo; or $R^1$ and $R^2$ taken together are methylenedioxy or ethylenedioxy; or $R^2$ and $R^3$ taken together are methylenedioxy or ethylenedioxy;

$R^3$ is H, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo; or $R^2$ and $R^3$ taken together are methylenedioxy or ethylenedioxy; or $R^3$ and $R^4$ taken together are methylenedioxy or ethylenedioxy; and $R^4$ is H, halo, cyano, nitro, $(C_1-C_6)$alkyl, $(C_3-C_6)$cycloalkyl, $(C_1-C_6)$alkoxy, $(C_1-C_6)$alkanoyl, $(C_1-C_6)$alkoxycarbonyl, methylenedioxy, ethylenedioxy, or $(C_2-C_6)$alkanoyloxy, wherein any $(C_1-C_6)$alkyl, $(C_3-C_6)$cycloalkyl, $(C_1-C_6)$alkoxy is optionally substituted with one or more halo; or $R^3$ and $R^4$ taken together are methylenedioxy or ethylenedioxy;

or a salt thereof.

2. The compound of claim 1 which is a compound of formula (Ia):

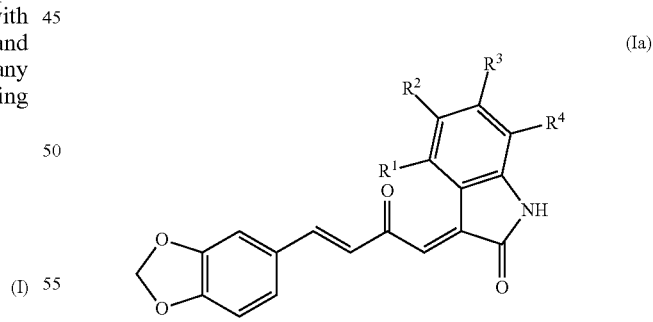

(Ia)

or a salt thereof.

3. The compound of claim 1 wherein ring A is substituted with one or more $(C_1-C_6)$alkoxy.

4. The compound of claim 1 wherein ring A is 3,4,5-trihydroxyphenyl or 4-nitrophenyl.

5. The compound of claim 1 wherein at least one of $R^1$, $R^2$, $R^3$, and $R^4$ is other than H.

6. The compound of claim 1 wherein at least one of $R^1$, $R^2$, $R^3$, and $R^4$ is halo, cyano, nitro, $(C_3-C_6)$cycloalkyl, $(C_1-C_6)$alkoxy, $(C_1-C_6)$alkanoyl, $(C_1-C_6)$alkoxycarbonyl, or $(C_2-C_6)$alkanoyloxy.

7. The compound of claim 1 wherein at least one of $R^1$, $R^2$, $R^3$, and $R^4$ is halo.

8. The compound of claim 1 wherein at least one of $R^1$, $R^2$, $R^3$, and $R^4$ is fluoro or chloro.

9. The compound of claim 1 wherein $R^2$ is halo.

10. The compound of claim 1 wherein $R^2$ is fluoro or chloro.

11. The compound of claim 1 wherein $R^3$ is halo.

12. The compound of claim 1 wherein $R^3$ is fluoro or chloro.

13. A compound selected from:

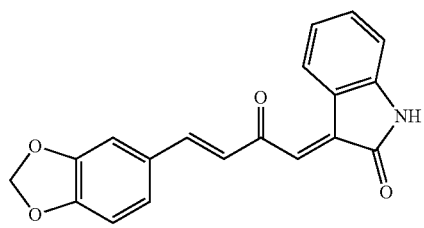

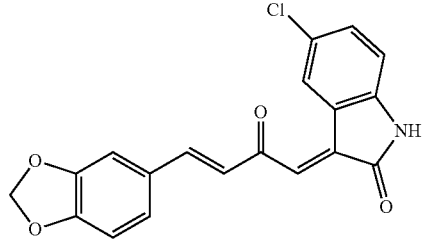

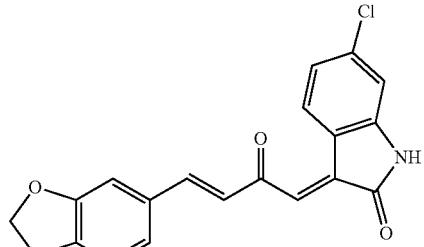

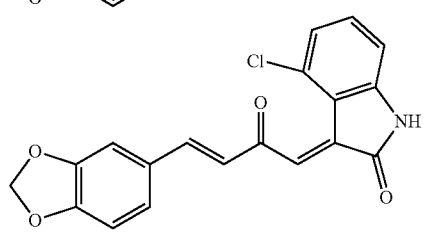

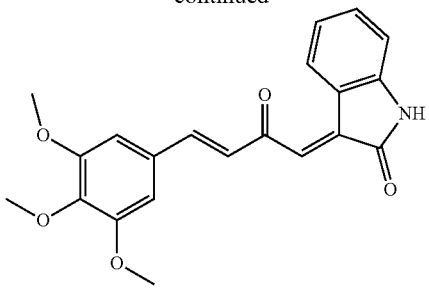

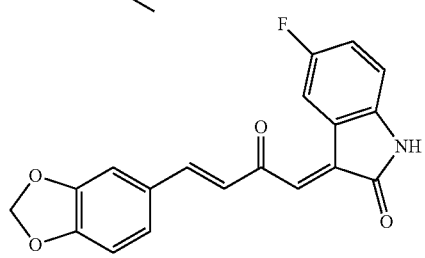

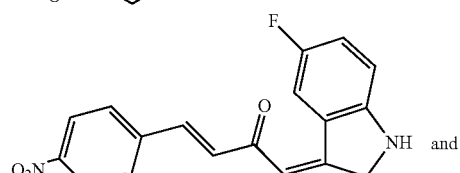 and

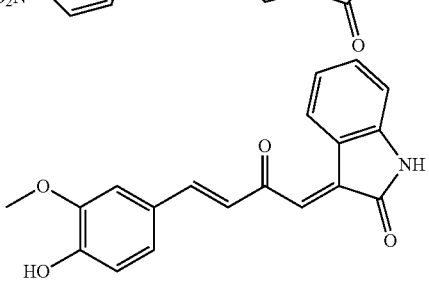

and salts thereof.

14. A pharmaceutical composition comprising a compound as described in claim 1 or a pharmaceutically acceptable salt thereof, and a pharmaceutically acceptable carrier.

15. A method of inhibiting Aurora B kinase in an animal in need of such treatment comprising administering a compound as described in claim 1 or a pharmaceutically acceptable salt thereof to the animal.

16. A method of treating a pathological condition associated with Aurora B kinase in an animal comprising administering an effective Aurora B kinase inhibitory amount of a compound as described in claim 1 or a pharmaceutically acceptable salt thereof to the animal.

17. A method of treating cancer in an animal comprising administering a compound as described in claim 1 or a pharmaceutically acceptable salt thereof to the animal.

* * * * *